(12) United States Patent
Costello et al.

(10) Patent No.: US 8,007,991 B2
(45) Date of Patent: Aug. 30, 2011

(54) THREE-DIMENSIONAL PHYSIOLOGICAL MATRICES FOR ONCOLOGICAL TESTING, AND METHODS FOR THEIR PRODUCTION AND USE

(76) Inventors: Penelope Catherine Costello, London (CA); Warren Bruce McDonald, London (CA)

( * ) Notice: Subject to any disclaimer, the term of this patent is extended or adjusted under 35 U.S.C. 154(b) by 130 days.

(21) Appl. No.: 11/812,128

(22) Filed: Jun. 15, 2007

(65) Prior Publication Data

US 2008/0070269 A1 Mar. 20, 2008

Related U.S. Application Data

(60) Provisional application No. 60/813,689, filed on Jun. 15, 2006, provisional application No. 60/929,122, filed on Jun. 13, 2007.

(51) Int. Cl.
*C12N 5/071* (2010.01)
*C12N 5/09* (2010.01)

(52) U.S. Cl. ............................ 435/1.1; 435/374; 435/375

(58) Field of Classification Search ......................... None
See application file for complete search history.

(56) References Cited

U.S. PATENT DOCUMENTS 5,712,161 A 1/1998 Koezuka et al.

FOREIGN PATENT DOCUMENTS

WO WO02/20825 * 3/2002

OTHER PUBLICATIONS

Bergstraesser et al (Cancer Research, 1993, vol. 53, pp. 2644-2654).*

Drug Facts and Comparisons,(1999 Edition, Kastrup et al, Ed.s, pp. 3286, 3288, and 3296).*
Schor et al (British Journal of Cancer, 1982, vol. 29, pp. 57-62).*
Freshney (The Culture of Animal Cells, Third Edition, 1994, pp. 58 and 81-83).*
Takamura Y. et al; "Production Of Chemotherapeutic Response By Collagen Gel Droplet Embedded Culture—Drug Sensitivity Test In Human Breast Cancers." Int. J. Cancer Mar. 20, 2002, vol. 98, pp. 450-455. ISSN: 0020-7138.
Koshida, K, et al.: "In Vitro Chemosnsitivity Test For Human Genitourinary Tumours Using Collagen Gel Matrix." Int. J. Urol. Jan. 2005; vol. 12, pp. 67-72. ISSN: 0919-8172.
Costello, P. et al.: "Screening For Tumour Therapy Sensitivity Using An Ex Vovo Invasion Assay." Neuro. Oncol. Oct. 2006, vol. 8, p. 440, abstract No. TA-11. ISSN 1522-8517.
Costello, P. et al.: "Determination Of Human Brain Tumour Therapy Response Using An Ex Vivo Invasion Assay Provides A Potential Step Toward Individualized Treatment," J. Clin. Oncol. 20-Jun.-206, vol. 24 (18S) abstract No. 11509. ISSN: 0732-183X.

* cited by examiner

*Primary Examiner* — Karen A Canella
(74) *Attorney, Agent, or Firm* — Gary L. Shaffer

(57) ABSTRACT

Three-dimensional physiological matrices, methods, apparatus and kits for the expedited design, testing and evaluation of oncological remedies are provided. Key aspects of the inventions include matrices, and especially gel matrices, comprising one or more physiological fibers, which are adapted and arranged to provide conditions which permit behaviors, such as the movement of cells away from the margins of samples of target tissue through the matrix, to be evaluated in a manner that produces data useful for evaluating the oncological status and characteristics of the cells. In a further key aspect, the invention permits the in vitro testing and analysis of one or more conventional, experimental or theoretical therapies with respect to specific target tissues or cells. Among such therapies are therapeutic compounds and combinations thereof, radiation therapies, combinations of therapeutic compounds and radiation and numerous other possible therapies.

41 Claims, 4 Drawing Sheets

CHEMOTHERAPY SCREEN Figures

Figure 1:
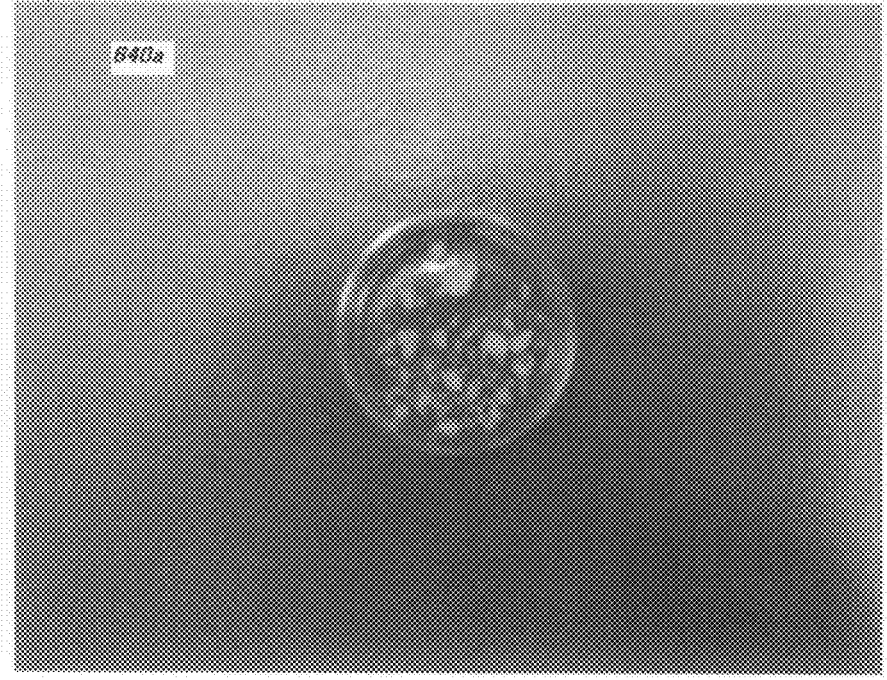

THREE-DIMENSIONAL PHYSIOLOGICAL MATRICES FOR ONCOLOGICAL TESTING, AND METHODS FOR THEIR PRODUCTION AND USE

PRIORITY STATEMENT

Applicants hereby claim priority to U.S. Provisional Patent Application Ser. No. 60/813,689, filed Jun. 15, 2006, and to U.S. Provisional Patent Application Ser. No. 60/929,122, filed Jun. 13, 2007, and entitled Three-Dimensional Physiological Matrices, Methods, Apparatus And Kits For The Expedited Design, Evaluation, Data Organization And Reporting With Respect To Oncological Remedies And Therapies. All the materials and information provided in the above-identified applications are hereby incorporated by reference.

FIELD OF THE INVENTION

The present invention relates to matrices, methods, apparatus and kits for the expedited design and evaluation of oncological remedies. Key aspects of the inventions include matrices, and especially gel matrices, which are adapted and arranged to provide conditions which permit behaviors, such as the movement of cells from a sample of target tissue, to be evaluated in a manner that produces data useful for evaluating the oncological status of the cells. In a further key aspect, the invention permits the in vitro testing and analyses of one or more therapies, such as therapeutic pharmaceutical compounds, or radiological therapies, with respect to specific target tissues and cells removed from a patient.

BACKGROUND OF THE INVENTION

Cancer is the loss of control of one or more of the regulatory systems which regulate the growth of cells and tissues. An uncontrolled growth of a particular tissue or cell type is a specific type of cancer. There are many types of cancer. In the treatment of cancer, one or more therapeutic remedies are typically used in attempts to cure the disease or ameliorate its effects. Many differences exist between classes of tumors and, indeed, individual tumors of the same type. There are many possible therapies for cancers in general. Nonetheless, most therapies do not work, or do not work to the extent necessary to provide the degree of cure, remediation or desired palliative effect for a specific cancer. Because of this, it is sometimes difficult, time-consuming and expensive to attempt to determine what therapeutic compounds may be effective to treat a particular tumor or cancer type. Oncologists and other physicians therefore often choose a therapy based on little or no pragmatic information regarding the specific tumor. In effect, their determinations of which therapy or therapies to employ are often guesses. It is therefore very important to be able to more effectively match a specific effective therapy to a specific tumor, and to be able to do so in a reasonable amount of time. As a consequence of these needs, many technologies have attempted to address these needs, but none have been acceptably successful.

Various experiments have been directed toward measuring the effects of certain therapies on malignant cells in vitro. One of these attempts is shown in "Effects of Radiation on a Three-Dimensional Model of Malignant Glioma Invasion" International Journal of Devl. Neuroscience, Vol. 17, issue 5-6, 643-651, August 1999, (Bauman et al.). The Bauman et al. researchers used suspensions of an established cell line, the C6 astrocytoma line, to show that the three-dimensional migration of known, cultured malignant cells into a collagen matrix could be observed. The malignant glioma cells thus cultured, disrupted and processed into cloned spheroids, which were then implanted into a gel matrix, and then subjected to one or more doses of fractionated radiation. Changes in the distance of invasion in response to single dose and fractionated radiation were measured over a period of 5 days.

Similar experiments were reported in "Effects Of Radiation On A Model Of Malignant Glioma Invasion", Journal of Neuro-Oncology 44: 223-231, 1999, (Baumann et al.). In this reference, the Baumann et al. researchers used the same C6 cell line and experiment-al protocols to test BCNU and dexamethasone, and to compare these results with those of radiation dosing on the transformed cells.

Significantly, in both series of experiments reported by Bauman et al., the cloned C6 astrocytoma cells were subjected to disruption by trypsinization, and also subjected to centrifugal forces for 3-4 weeks in spinner flasks. Thus, the cells of Bauman et al were already known to be transformed to a great extent, were generations removed from the original tissue, required disruptive chemical processing, and were a subset of cloned malignant cells at the time they were subject to radiation doses. C6 astrocytoma cells were maintained in tissue culture as cloned representatives of malignant rat glioma cells. Indeed, the cells of the Bauman et al. experiments were removed and established as a cell line years before they were subjected to the experiments of Bauman et al.

In significant contrast, the present invention uses a sample quantity of fresh tissue taken directly from an animal, such as a human patient. Significantly, the samples used in the present invention are not disrupted by trypsin or other enzymes, but are mechanically divided into sample portions of appropriate sizes for testing. Thus, the present methods maintain the cell-to-cell contact of the sample tissue as if it were still in vivo. An additional difference pertains to the fact that the experiments of Bauman et al. used an established cell line, that is, cells that were already known to have been transformed long before, and in an unknown way, to an extent great enough that they could be used to establish a tissue culture cell line. One could not therefore expect the cells of Baumann et al. to behave in a manner reasonably replicative of fresh or in vivo cells.

Others have attempted to provide ways of evaluating the response of tumor cells to chemotherapeutics. In U.S. Pat. No. 5,242,806 to Yen-Maguire et al., entitled Method For Conducting The Cytotoxicity Assays On Tumor Cells, a "growth matrix" of bovine cornea endothelium cells is sometimes employed as a coating in the wells of multi-well plates in order to facilitate the attachment of cells to the plate surfaces. Essentially, Yen-McGuire discloses ways of culturing cellular suspensions which have been grown in two dimensions, and then assaying the responses of the processed cells to various cytotoxic or chemotherapeutic compounds.

The cellular suspensions of Yen McGuire are provided with a defined, selective growth medium which is designed and formulated to promote the growth of epithelial tumor cells while inhibiting the growth of normal cells. Yen-McGuire thus teaches the use of selective nutrition to skew cellular growth and behavior. Indeed, the relative amount of cellular growth is measured to provide information regarding the sensitivity of the highly processed tumor cells. Thus, Yen-McGuire does not provide any analysis with respect to an original tumor sample or fragment thereof, nor does it comprehend the advantages of an in vitro system which replicates significant aspects of the three-dimensional environment of tumor tissue in vivo.

These problems regarding the lack of analytic tools which are effectively usable to provide information specific to particular tumors, combined with the fact that cancer often progresses rapidly, have created a significant need for means and methods to quickly obtain information useful for testing and evaluating specific therapies, for example, therapeutic compounds, to determine their effectiveness with respect to particular tumors or cancer types. There is thus a significant need for such means and methods.

SUMMARY OF THE INVENTION

Accordingly, it is an object of the present invention to remedy the above-mentioned drawbacks by providing three-dimensional matrices, such as gels, as well as methods and kits for evaluating and testing tissue and cells to determine if they are abnormal, pre-cancerous, or cancerous.

Another object of the present invention is to provide methods and kits for testing one or more therapeutic substances to determine their efficacy against a particular tumor or type of tumor.

In accordance with these and other objects, and in accordance with the context of the invention with respect to providing novel and non-obvious improvements in all relevant fields, multiple means and methods of practicing the inventions are provided.

In accordance with these and other objects, means and methods for evaluating the oncological characteristics of at least one tissue or cells from an animal, such as a human being, which cells or tissue are suspected of being abnormal, cancerous or pre-cancerous, are provided. In one preferred embodiment, a method of the invention comprises the steps of A) obtaining a sample quantity of the suspected tumor tissue or cells from the animal, wherein the tissue comprises one or more types of cells, B) implanting at least part of the sample of the suspected tumor tissue at least partially within a three-dimensional physiological matrix, the matrix being adapted and arranged for measuring one or more parameters of the behavior of the cells of the suspected tumor tissue, C) providing sufficient nutrition to the cells of the tissue or cells so that the parameters can be measured, D) incubating or culturing the tissue and the cells in an environment suitable for the growth of the cells and the tissue for a time sufficient to obtain measurements with respect to one or more parameters, and E) measuring some of those one or more parameters to obtain data regarding those behaviors.

Methods of the present invention are further adapted such that, preferably, the implantation of the sample, or portions thereof, is effected with minimal disruption to the cells or the tissue. For example, in a typical procedure according to some preferred embodiments of the invention, a sample quantity of a tissue is removed from a patient by way of a biopsy or surgery. The structural integrity of that tissue sample is then maintained to the maximum extent possible before its implantation. In this regard, it is noteworthy that non-disruption of the sample means, as examples, that the sample is not homogenized, it is not chemically disrupted by strong acids, or by enzymes such as trypsin, nor is it comminuted, crushed or subjected to high concentrations of strongly basic compounds. In sharp contrast, a sample according to the invention is cut, torn or chopped into small pieces, such as chunks approximating cubes of 1.0-3.0 mm on an edge. While not intending to be bound by any underlying mechanism, the present inventors theorize that, by minimizing the disruption to the sample tissue and cells, their respective behaviors in relation to a physiological matrix of the invention remains similar to their corresponding behaviors in vivo.

In this same vein, it is preferable that implantation of the samples during the methods of the invention take place as soon after the sample is removed from the animal as is reasonably possible. Thus, a removed tissue sample is preferably immediately cooled by placing it in proximity to ice, for example, and implantation is most preferably accomplished within one or a few hours after removal. Although implantation is most preferably accomplished within an hour or so of sample removal, the present methods provide for later implantation when circumstances dictate as much, such as when the sample must be transported some distance to a laboratory for preparation. In any event, implantation should most preferably take place within four hours of removal of the sample tissue, or more preferably within 24 hours of removal, and less preferably within 48 hours of removal of the tissue from the subject animal. As one of skill in the oncological arts will appreciate, the effects of the delay in implantation and evaluation of a tissue sample may depend upon many factors, including the type of tissue, its oncological status, and the conditions under which it has been stored. Thus, it may be possible to delay implantation for many hours or many days.

As another advantage of the invention, its means and methods provide data for physicians and other evaluators to make determinations or estimates regarding the oncological status of a tissue and its cells. Thus, from the data obtained, a determination can be made regarding whether the tissue and cells are abnormal, pre-cancerous or cancerous. As a further advantage, the present means and methods permit the testing of many types of therapies, including pharmaceutical compounds and non-chemical therapies. The present means and methods can therefore be used to provide data useful for tailoring specific individual therapeutic regimens directed toward the precise tissue being evaluated. To this end, some preferred embodiments of the present invention further comprise the step of transmitting the data to at least one evaluator. In the context of the invention, an evaluator is any person, group of people, or network of people, or any machine, computer or device adapted and arranged for evaluating the data garnered through use of the present means and methods. Evaluators include, but are not limited to the group comprising technicians, technicians, physicians, physician's staff members, physician's assistants, hospital employees, clinic employees, the patient, technologists, technical assistants, laboratory assistants, oncological analysts, nurses, nurses' assistants nurse practitioners, computers, computer-aided devices, computer-facilitated devices, and human or computerized agents for any of the foregoing.

In accordance with still further aspects of some preferred embodiments of the invention, the removed sample quantity of tissue is divided into a plurality of portions, and each of the portions is subjected to the some or all steps of the invention. Thus, tests and evaluations of the tissue and cells can be performed in multiples, and one or more therapies can be tested concurrently in relation to the specific sample if desired.

Moreover, the measurements taken with respect to each portion of a sample are taken over time, either at periodic intervals, or at random intervals. In some preferred embodiments therefore, Step E is performed more than once, or a plurality of times with respect to the separate portions of the sample. Preferably, these measurements are effected during the culturing or incubating of the tissue and cells as in Step D above.

Advantageously, means and methods of the invention can be used on virtually any type of animal, including human medical patients, and can be used also to evaluate tissue from other animals. Other animals include, but are not limited to non-human primates, equines such as horses and donkeys, bovines such as cows and deer, canines such as dogs and wolves, felines such as lions and domestic house cats, murines such as mice and moles, porcines such as pigs and peccaries, avians such as birds and penguins, amphibians such as salamanders and turtles, and reptilians such as snakes and alligators. The animals mentioned herein comprise an exemplary listing, and not an exclusive one.

Methods of the invention also include where the measurements taken, as in Step E, are performed more than once with respect to each of the separate portions of the sample, and wherein the measuring is effected during the culturing or incubating of Step D. A significant aspect of the invention concerns the physical relationship between the tissue sample portion and the three-dimensional matrix in which it is implanted. Preferably, the tissue portion is disposed either partially submerged in the matrix, or completely submerged therein. It is important that the tissue be in intimate contact with the matrix. Thus, the physiological matrix replicates to some extent the three-dimensional environment in which most tissues function in vivo. Tissue samples, or portions thereof, may be implanted in any method, manner or way, which yields the desired results As an aid to implantation, the matrices of the invention, which are typically gels or other permeable solids or semi-solids, can be provided in shapes which facilitate the implantation of one or more types of tissues and cells, and which facilitate the provision of nutrition to the cells and tissue. Thus, any type of depression such as a hollow, cavity, slit, chamber or slot can be provided within the matrix itself, and can be adapted and arranged to receive the tissue or cells for implantation, or can be adapted and arranged to hold nutrition for the cells and tissue. For example, a gel matrix according to the invention may comprise a hollow, cavity, slit, chamber or slot of an appropriate volume and disposition to receive an aliquot, such as a 0.2 ml. aliquot of 10× media, as nutrition for the implanted cells and tissue. Such depressions can also serve as receptacles or reservoirs for drugs to be tested.

In some preferred embodiments of methods of the invention, the tissue or cells are implanted in the matrix as the matrix is being formed into a gel or other permeable solid or semi-solid. In these embodiments, the tissue and cells are mixed along with the components of the matrix and are thus partially or completely submerged within the matrix by the time it gelates or hardens into a semi-solid or solid. In those preferred embodiments where the matrix is already formed, the tissue or cells can be implanted in the matrix by physical insertion after it has formed into a gel, solid or semi-solid.

It is important to note that solutions for forming matrices of the invention should be essentially free of bicarbonate. By maintaining this bicarbonate-free condition, the gels or semi-solids of the invention advantageously form at room temperatures and are thus capable of being mixed and formed in a manner that is convenient, user friendly, and adaptable to many laboratory and non-laboratory environments.

In accordance with other aspects of the invention, sufficient nutrition is provided to the cells and tissue to be evaluated or tested, either as a component of the matrix as it is being formed, or as nutrition added after the matrix is formed, or both. The nutrition must be sufficient to grow the cells and tissue for a sufficient length of time to obtain the desired results. In some embodiments, the sufficient or additional nutrition preferably comprises one or more fluids, wherein the one or more fluids are selected from the group comprising tissue culture medias, concentrated tissue culture medias, and any culture or nutritional medias which are suitable for the tissue sample. The means and methods of the present invention thus include wherein the concentrated medias are one or more selected from the group comprising 10× medias, and any other concentrated medias.

In another aspect of the invention, the three-dimensional physiological matrix comprises the sufficient nutrition as a component of the matrix itself as it is being mixed and formed or allowed to gel. As a further aspect of the invention, a step of providing at least one source of additional nutrition to the tissue and the cells is provided. Thus, the tissues and cells may avail themselves of one or both of the sufficient nutrition and of the additional nutrition to the extent necessary so that the parameters can be measured. In accordance with similar aspects of the invention, the at least one source of additional nutrition may comprise one or more of tissue culture medias, concentrated tissue culture medias, and any culture or nutritional medias which are suitable for the tissue sample. As a further aspect of the invention, the at least one additional source of nutrition may be supplemented with one or more components selected from the group comprising sera, proteins, sugars, salts, lipids.

A further method of the present invention wherein the measuring of Step E is performed at periodic intervals. Preferably the measuring step is performed at periodic intervals such as one or more intervals selected from the group comprising every six hours, every 12 hours, every 18 hours, every 24 hours, every 36 hours, every 48 hours, every 72 hours and every 96 hours. Moreover other intervals are one or more selected from the group comprising every day, every second day, every third day, every fourth day, and every fifth day.

As another advantage, the data obtained by the measurements of the invention is recorded in a fixed media. Such fixed media can be any type so long as it is capable of holding the obtained data in such form as to be useable later. For example, paper, voice recordings, video recordings, photographs, photomicrographs, digital recordings, any fixed digital data means. According to the invention one or more of a human observer, a still camera, a video camera, an automated still camera, an automated video camera, an infrared camera, and an automated infrared camera can be used to obtain the desired data.

Preferably the culturing of tissues and cells according to the invention occurs in a period of time sufficient to obtain the desired parameters and values. For example, the periods of time during which the culturing of tissues and cells is effected includes those of at least 10 hours, at least 36 hours, at least 72 hours and at least 125 hours, or even longer depending on the conditions of the tissue and how the method is being conducted In accordance with other aspects of the invention, the sufficient nutrition is provided to the tissues and cells by placing the sufficient nutrition in contact with the matrix after the sample has been placed in the matrix and the matrix has equilibrated to room temperature, and to a semi-solid or gel. Preferably, the room temperature is in the range of from 10 to 30 degrees Celsius. In accordance with other aspects, the sufficient nutrition may be provided to the tissues and the cells by placing the it in contact with the matrix after the sample has been placed in the matrix, and the matrix has equilibrated to a gel at room temperature. In other embodiments, the sufficient nutrition may be provided to the tissues and the cells by continuous or intermittent perfusion or flow over, around, or through the matrix. In yet another aspect, the three dimensional quality of the matrix of the invention can be formed itself to comprise the sufficient nutrition. The environment for incubating or culturing the cells and the tissue preferably includes a temperature range of from 30 to 40 degrees Celsius, a carbon dioxide tension of from 2 to 13%, and a relative humidity of from 50% to 100%.

In accordance with other aspects, methods of the invention can be conducted wherein the sample quantity is preferably divided into portions, and each of these portions is subjected concurrently and separately to the method, wherein the matrix comprises a gel, and wherein the gel is suitable for measuring the one or more parameters to obtain the desired values. Thus, multiple equivalent matrices may be formed in multiple containers, such as multiple containers comprising a multi-well apparatus, such that multiple portions of the sample can be evaluated concurrently. Thus, the present invention includes where a particular tissue can be evaluated at multiple times, with respect to multiple portions of the sample, and with respect to multiple therapies.

Advantageously, the present invention can be used to measure or obtain data with respect to one or more parameters regarding the behavior of the cells and tissue. Those parameters include one or more of the distance which individual cells migrate from the tissue sample, the average distance of migration of a group or population of the cells from the tissue sample, the distance which individual cells migrate from the tissue sample with respect to time, the average distance of migration of a group or population of the cells from the tissue sample with respect to time, the velocity of migration of one or more designated individual the cells per selected time period, the velocity of migration of a group or population of designated the cells per selected time period, the number of migrational cells per unit area of a microscopic visual field, the speed of proliferation of the cells, the speed of unidirectional migration of the cells, the speed of bi-directional migration of the cells, the speed of tri-directional migration of the cells, the frequency of directional change of the migrating cells, the number of directional changes per unit time of the migrating cells, the rate of mitosis of the migrating cells, the number of cells migrating per unit time, the number of cells in a unit area of a portion of the gel, the change in the number of cells in a unit area of a portion of the gel with respect to time, the number of cells in a unit volume of a portion of the gel with respect to time, and the change in the number of cells in a unit volume of a portion of the gel, the proportion of cells which change migrational direction during the test period, the speed of migrating cells in a particular visual field, the density of migrating cells per unit area of a visual field, the migrational distance of individual migrating cells per unit area of a visual field, the average migrational distance of a group or population of migrating cells per unit area of a visual field, osmotic pressure, ionic strength, the change in pH with respect to time, the change in pH with respect to the amount of cell migration, oxygen consumption, glucose consumption, and the number of migrating cells in a particular direction per unit area of a visual field.

In accordance with other advantageous aspects of the invention the three-dimensional physiological matrices for use with the invention can be adapted and arranged to have whatever pH value or range necessary to culture and evaluate the specific target tissues and cells. Preferably, the pH range for testing most tissues is from 5.0 to 8.0, and, more preferably, from 7.0 to 7.5. Thus, the physiological matrix preferably has a pH which is adapted to a range suitable for one or more of a particular tissue, a particular cell type or types, or to a particular tumor.

Preferably, a three dimensional matrix of the invention comprises at least one natural or synthetic fiber, for example, one or more fibers selected from the group including type I collagens, type II collagens, type III collagens, type IV collagens, fibrin, fibrinogen, extracellular matrix proteins derived from one or more animals, laminin, fibronectin, anti-laminin, and other natural or synthetic fibers or cables suitable to the formation of a matrix mesh or network capable of supporting cell support, movement and growth. In some preferred embodiments a physiological matrix according to the invention preferably comprises a gel, the gel being suitable for measuring at least one or more of the parameters necessary for evaluating the tissue, the cells, possible therapies, and is also adapted and arranged for measuring the efficacy of one or multiple therapeutic compounds.

The means and methods of the present invention are especially adapted and arranged to test the efficacy of virtually any therapy regimen, including pharmacologic therapeutics. In one context therefore, a physiological matrix of the invention is adapted and arranged for measuring the efficacy of one or more therapeutic compounds, such as known and unknown single compounds, and known and unknown therapeutic cocktails. As examples, and not as an exclusive listing, one or more therapeutic compounds for use or evaluation in the context of the invention may be selected from the group comprising anti-tumor agents, DNA damaging agents such as alkylating agents, antibiotics which affect nucleic acids, platinum compounds, anti-mitotics, cell cycle stimulators, anti-metastatic agents, anti-metabolites, camptothecin derivatives, hormone therapies, biological response modifiers, interferon, anti-invasives, anti-invasion agents, anti-migration agents, anti-angiogenesis agents, and apoptotic agents, radiosensitizers, radiation, and any known, theoretical or experimental therapeutics directed against cell growth, cell invasion or cell viability, pro-tumor agents, pro-mitotic agents, pro-metastatic agents, pro-invasion agents, pro-migration agents, pro-angiogenesis agents, and anti-apoptotic agents.

More specifically, the three-dimensional physiological matrices of the invention may be adapted and arranged for measuring the efficacy of one or more therapeutic compounds, such as those selected from the group comprising Temozolomide (TMZ), Irinotecan, Procarbazine, Methotrexate, Carboplatin, Adriamycin Cisplatin, Vincristine, Paclitaxel, 1-(2-chloroethyl)-3-cyclohexyl-1-nitrosourea (CCNU), carmustine (BCNU), Cyclophos-phamide, Docetaxel, fluorouracil (5FU), Cytarabine, doxorubicin, bleomycin, topotecan, tamoxifen (TMX), and imatinib mesylate (Gleevec) and all other therapeutics shown to be appropriate for treatment.

As additional examples, a physiological matrix of the invention is adaptable for measuring one or a cocktail of therapeutic compounds comprising one or more, or at least two compounds selected from one or more of CAF (Cyclo-phosphamide/Adriamycin/Fluorouracil); CMF (Cyclophos-phamide/Methotrexate Fluorouracil); CMFVP (Cyclophos-phamide/Methotrexate/Fluorouracil/Vincristine/
Prednisone); PCV (Procarbazine/CCNU/Vincristine); ICARBO-E (Ifosfamide/Carboplatin/Etoposide); TAP (Taxol/Adriamycin/Cisplatin); EMA-CO (Etoposide/Methotrexate/Actinomycin/Cyclophosphamide/Vincristine);
VBP (Vinblastine/Bleomycin/Platinol (Cisplatin)); BPD-T: (Bcnu/Platinol/Dacacarbazine/Tamoxifen); and T-10 (Methotrexate/Bleomycin/Cyclophosphamide/Dactino-mycin/
Adriamycin), Dactinomycin/Adriamycin) and any other actual or theoretical therapeutics which might be appropriate for treatment.

As yet another advantage, the means and methods of the invention may be adapted and arranged to test the efficacy of non-chemical therapies. As examples, and not to be taken as an exclusive listing, non-chemical therapies subject to being evauated or tested in the context of the present invention include one or more selected from the group comprising radiation therapies, brachiotherapies, herbal therapies, naturopathic therapies, experimental therapeutic compounds, and new therapeutic compounds.

In additional aspects, the method may further comprise the step of determining the oncological status of the cells of the removed tissue from the data thus obtained. Preferably, the methods may further comprise the step of recording the data in some fixed media so that it can be analyzed, communicated to others, and used as a record of the procedures and their results.

In accordance with other objects of the invention, methods for evaluating the efficacy of one or more therapeutic compounds with respect to one or more tissues comprising cells from an animal are provided. Methods of the invention are particularly relevant with respect to tissue and cells which are suspected of being abnormal, cancerous or pre-cancerous. Indeed, the present means and methods are especially adaptable to testing or evaluating one or multiple therapeutic compounds with respect to specific tissue and cells. As a result of this ability to evaluate potential therapies, such as therapeutic compounds, with respect to an exact tissue, time, effort and expense are saved in terms of the determination of an appropriate therapeutic regimen.

In one preferred embodiment, the present methods for evaluating one or multiple therapeutic compounds comprises the steps of A) obtaining a sample of the suspected tissue from the animal, wherein the tissue comprises one or more types of cells, B) implanting a portion of the sample of the suspected tissue at least partially within a three-dimensional physiological matrix, the matrix being adapted and arranged for measuring one or more parameters of the behavior of the tissue and the cells, C) providing sufficient nutrition to the cells and the tissue so that the parameters can be measured, D) providing at least one of the one or more therapeutic compounds to the cells and the tissue, E) incubating or culturing the tissue and the cells with the one or more therapeutic compounds in an environment suitable for the growth of the cells and the tissue, and for a time sufficient to obtain measurements with respect to the one or more parameters, and F) measuring one or more of the parameters to obtain data regarding the behaviors with respect to the one or more therapeutic compounds.

Advantageously, the methods may further comprise the step of, from the data thus obtained, determining the efficacy of the one or more therapeutic compounds with respect to the tissue and the cells. Preferably, methods of the invention may further comprise the step of recording the data in some fixed form, and may further comprise the step of transmitting the data to at least one evaluator. Evaluators and the recordation of data obtained by the present means and methods are also discussed herein.

The invention is also especially adapted for circumstances wherein the sample quantity is divided into portions, and each of the portions is subjected concurrently and separately to the method, wherein the method includes the use of one or more controls adapted for evaluating the one or more therapeutic compounds. Thus, the present methods can include the use of one or more controls adapted for evaluating the one or more therapeutic compounds with respect to the particular tissue, and with respect to specific conditions created by the test or testing lab or clinic. Methods of the invention also include where Step D is performed during Step E, and wherein the measuring of Step F is performed more than once with respect to each of the separate portions of the sample, and wherein the measuring is effected during the culturing or incubating of the tissue and cells. Preferably, the tissue portion is disposed either partially submerged in the matrix, or completely submerged therein.

It is important that the tissue be in intimate contact with the matrix. Thus, the physiological matrix replicates to some extent the three-dimensional environment in which most tissues function in vivo. Tissue samples, or portions thereof, may be implanted in any method, manner or way, which yields the desired results. Means and methods of the invention can be used also where the implanted tissue is obtained from one or more of a liquid tissue, a cell suspension, cells or groups of cells which have been palletized, and wherein the tissue or cells are implanted in the matrix after the matrix has formed into a gel or other permeable solid or semi-solid.

Means and methods of the invention can be used with virtually any animal tissue as described herein. Moreover, it is important to note that matrices of the invention should be essentially free of bicarbonate when the matrix is being formed into the gel, semi-solid or permeable solid. As an additional advantage, methods of the invention can be practiced with respect to one or more therapeutic compounds, for example where a single compound is tested and the method is performed with at least one set of controls. As one skill in the art of testing oncological remedies will appreciate, any number of controls, therapeutic substances, therapeutic methods, experimental compounds, or other cancer treatments such as radiation, radiotherapy or any other actual, theoretical or experimental therapy of method can be tested with the present invention in in vitro conditions.

Moreover, therapeutic compounds can be provided to the tissues and cells as a component of the sufficient nutrition. More therapeutic compounds are provided to the cells and the tissue as a component of the physiological matrix. As a component after the sufficient nutrition is provided to the cells and tissues or wherein the one or more therapeutic compounds include two compounds and the method is performed with at least one set of controls. It is similarly possible to use the present invention and methods to test three or more therapeutic compounds preferably with respect to at least one set of controls. Methods of physiological matrix is adapted and arranged for measuring the efficacy of one or more therapeutic compounds, and wherein the one or more therapeutic compounds are selected from the group comprising DNA damaging agents such as alkylating agents, antibiotics which affect nucleic acids, platinum compounds, anti-mitotics, cell cycle stimulators, anti-metastatics, anti-metabolites, camptothecin derivatives, hormone therapies, biological response modifiers, interferon, anti-invasives, radiosensitizers, radiation, and any established, theoretical or experimental therapeutics directed against cell growth or cell invasion.

The present means and methods with respect to a three-dimensional physiological matrix of the invention are adapted and arranged for measuring the efficacy of one or more therapeutic compounds.

More specifically, a physiological matrix of the invention is adapted and arranged for measuring the efficacy of one or more therapeutic compounds comprises at least two therapeutic compounds. And where at least two therapeutic compounds are selected from one or more of It is again necessary to mention that the physiological matrices according to the invention should be essentially free of bicarbonate, for example wherein the matrix is formed from components that are essentially free of bicarbonate, and the final gel form of the matrix is thus essentially bicarbonate free.

As another distinct aspect of the present methods one or more parameters can be obtained regarding the behaviors of one or more therapeutic compounds, and the behaviors of the cells themselves. Parameters thus measured yield data. In turn, such data can be used to evaluate the performance of the cells, or the performance of one or more therapeutics, or the performance of one or more other types of therapies with respect to the tissues and cells tested. Preferably, the measuring step E is performed at periodic intervals, and wherein the periodic intervals are appropriate to one or more of the cells, the tissue and the therapy or therapies being tested or evaluated.

Preferably the measuring of Step E is performed at periodic intervals for a period of time of between one hour and 15 days. More preferably, the periodic intervals are one or more selected from the group comprising every six hours, every 12 hours, every 18 hours, every 24 hours, every 36 hours, every 48 hours, every 72 hours and every 96 hours. Moreover other intervals such as every day, every second day and every third day, every fourth day, every fifth, day every sixth day, every seventh day, every eighth day, and every ninth day. Methods of the present invention wherein the measuring of Step E is performed at non-periodic intervals, and wherein the non-periodic intervals are appropriate to one or more of the cells, the tissue and the therapy or therapies being tested or evaluated.

As another advantage, the data obtained by the measurements of the invention is recorded in a fixed communications media. Such fixed media can be any type so long as it is capable of holding the obtained data in such form as to be useable later. For example paper, voice recordings, video recordings, photographs, photomicrographs, digital recordings, any fixed digital data means, any computer network-facilitated means, infrared recording, ultrasound recordings, and magnetic resonance recordings. According to the invention one or more of a human observer, a still camera, a video camera, an automated still camera, an automated video camera, an infrared camera, and an automated infrared camera.

Preferably the culturing and/or incubating of tissues and cells according to the invention occurs for a period of time sufficient to obtain data regarding the desired parameters and values. For most tissue and cells to be tested, that period of time is between one hour and 15 days. More specifically, the culturing or incubating of the tissue and the cells typically occurs for a period of time of at least 1 hour, or at least 10 hours, or at least 24 hours, or at least 36 hours or at least 72 hours, or at least 125 hours, or at least 175 hours, or at least 200 hours, or at least 250 hours or at least 300 hours.

In some preferred embodiments, the environment for incubating or culturing the cells and the tissue includes a temperature range of from 26 to 43 degrees Celsius, a carbon dioxide tension of from 2.0% to 13.0%, and a humidity range of from 50-100%.

In accordance with other aspects of the invention, the sufficient nutrition comprises one or more fluids, and wherein the one or more fluids are selected from the group comprising tissue culture medias, concentrated tissue culture medias, and any culture or nutritional medias which are suitable for the tissue sample Preferably the concentrated medias are one or more selected from the group comprising 10× medias, and any other concentrated medias. Preferably, the sufficient nutrition is provided to the tissues and cells by placing the sufficient nutrition in contact with the matrix after the sample has been placed in the matrix The method of the invention further comprises the step of J) providing at least one source of additional nutrition to the tissue and the cells so that the parameters can be measured. Wherein at least one source of additional nutrition comprises one or more of tissue culture medias, concentrated tissue culture medias, and any culture or nutritional medias which are suitable for the tissue sample and wherein least one additional source of nutrition is supplemented with one or more selected from the group comprising sera, proteins, sugars, salts, lipids. Preferably the sufficient nutrition is provided to tissues and cells by placing the sufficient nutrition in contact with the matrix after the sample has been placed in the matrix and the matrix has equilibrated to room temperature, wherein the room temperature is in the range of from 10 to 30 degrees Celsius.

Advantageously, the present invention can be used to obtain data regarding one or multiple parameters of the behaviors of the tissue and cells being evaluated or tested as discussed herein. Significant among those parameters are the distance which individual cells migrate from the margins of the tissue sample, the average distance of migration of a group or population of the cells from the margins of the tissue sample, the distance which individual cells migrate from the tissue sample with respect to time, and the number of migrational cells per unit area of a microscopic visual field, that is, cell density in a portion of the gel.

As an additional advantage, methods of the invention may include those for evaluating the efficacy of one or more therapies with respect to at least one tissue from an animal, the tissue comprising cells, and the tissue being suspected of being abnormal, pre-cancerous or cancerous, the method comprising the steps of A) obtaining a sample of the tissue from the animal, wherein the tissue comprises one or more types of cells, B) implanting the sample at least partially within a three-dimensional physiological matrix, the matrix being adapted and arranged for measuring one or more parameters of the behavior of the cells of the tissue or cells, C) providing sufficient nutrition to the cells of the tissue of the portions so that the parameters can be measured, D) subjecting the cells and the tissue to at least one of the one or more therapies, E) incubating or culturing the tissue and the cells of the portions in an environment suitable for the growth of the cells and the tissue for a time sufficient to obtain measurements with respect to the one or more parameters for each of the portions, and with the one or more therapeutic compounds, F) measuring, with respect to each of the portions, one or more of the parameters to obtain data regarding the behaviors with respect to the one or more therapies.

In accordance with these and other objects of the invention, a three-dimensional physiological matrix suitable for culturing at least one tissue from an animal, the tissue comprising cells, is provided. In one aspect, the tissue or cells of the sample are suspected of being abnormal, cancerous or pre-cancerous. In another, the physiological matrix comprises A), at least one natural or synthetic fiber means, wherein the fiber means is adapted and arranged such that the cells, if abnormal, cancerous or pre-cancerous, are enabled to grow away from the sample into the matrix when the sample is implanted at least partially in the matrix, B), a sufficient amount of at least one additive comprising sufficient hydroxyl or hydrogen groups to bring the effective pH range of the matrix into an acceptable range, and C), sufficient nutrition to sustain the cells and the tissue in the matrix. It is important to note that the matrices of the invention and the sufficient nutrition should be essentially free of bicarbonate when they are being formed.

The three-dimensional physiological matrix is mixed from components and formed into a solid, a semi-solid, or a gel, and the matrix is adapted and arranged to permit migration of the cells away from the margins of the tissue and into the matrix. Moreover, the matrix is formulated, adapted and arranged to accept the sample as soon as the solid or gel is formed, or during its formation.

Preferably, a three-dimensional physiological matrices of the invention comprise at least one natural or synthetic fiber, for example, one or more selected from the group comprising type I collagens, type II collagens, type III collagens, type IV collagens, fibrin, fibrinogen, laminin, anti-laminin, positively charged poly(L-lysine)amino acid chains, positively charged poly(D-lysine)amino acid chains, and extracellular matrix proteins derived from one or more animals. In one preferred embodiment, the matrix comprises at least 90% Type I collagen. In another preferred embodiment of a matrix according to the invention, the gel comprises at least 95% Type I collagen.

The pH of a three-dimensional physiological matrix of the invention is brought into an acceptable range by means of one or more additives preferably selected from the group comprising NaOH, KOH and other strongly basic compounds. A matrix of the invention may further comprise additional nutrition to be added after the formation of the matrix into a solid, semi-solid or gel.

In accordance with other aspects of the invention, the sufficient nutrition comprises one or more fluids, preferably selected from the group comprising tissue culture media, concentrated tissue culture media or any culture or nutritional media which are suitable for the tissue sample to be evaluated. Suitable concentrated medias include one or more selected from the group comprising 10× media, and other concentrated media. Preferably, the sufficient nutrition is provided to the tissues and cells by placing the sufficient nutrition in contact with the matrix after the sample has been placed in the matrix and wherein one additional source of nutrition is supplemented with one or more selected from the group comprising sera, proteins, sugars, salts, lipids, and the matrix has equilibrated to room temperature, wherein room temperature is in the range of from 10 to 30 degrees Celsius.

In accordance with other advantageous aspects, a three-dimensional physiological matrix for use in the context of the invention can be adapted or arranged to have whatever pH value or pH ranges necessary to culture and evaluate the specific tissues and cells. Preferably, the pH range for testing most tissues is from 5.0 to 8.3, more preferably 6.4 to 7.9 and even more preferably from 7.4 to 7.6. Preferably, the tissue to be evaluated or tested is implanted or disposed completely submerged within the three-dimensional matrix.

In accordance with other aspects of the three-dimensional physiological nature of the invention, a matrix is preferably adapted and arranged to be in sufficient proximity to at least one additional source of nutrition, wherein the matrix is permeable to the additional source of nutrition to the extent necessary that the sample tissue and cells receive nutrition sufficient to enable them to grow into the matrix to the extent necessary to measure the one or more parameters. Moreover, the at least one additional source of nutrition may preferably include one or more additives or supplements selected from the group comprising serums, proteins, sugars, salts and lipids or any culture media that is suitable for the cell or tissue type. Preferably, the density of the fiber in a formed matrix of the invention is between 1.3 and 3.3 mgs/ml, more preferably from 2.0 to 2.8 mgs/ml, and even more preferably between 2.3 and 2.5 mgs/ml.

Advantageously, the present invention can be adapted and arranged to be suitable for measuring at least one parameter of the behavior of cells from the tissue, and at least one parameter relating to the suspected cancerous or abnormal status of the cells or the tissue. These parameters are listed hereinbefore.

In a significant aspect, a three-dimensional physiological matrix of the invention includes at least one natural or synthetic fiber selected from the group comprising Type I collagen, wherein the Type I collagen comprises at least 70% of the total fiber of the formed matrix, or at least 80% of the total fiber, at least 90% of the total fiber and at least 95% of the total fiber. In one preferred embodiment, a three-dimensional physiological matrix of the invention comprises at least one natural or synthetic fiber means of primarily Type I collagen, and at least one additive sufficient to bring the pH of the matrix into an acceptable range, such as a sufficient amount of 0.1 N NaOH, and wherein the sufficient nutrition is a bicarbonate-free 10× media.

In another preferred embodiment, a three-dimensional physiological matrix of the invention comprises eight parts by volume of the natural or synthetic fiber, the at least one additive comprises one part by volume of the 0.i N NaOH, and the sufficient nutrition comprises one part by volume of the bicarbonate-free 10× media.

In another aspect, a physiological matrix according to the invention may comprise at least one first hollow, cavity, slit or chamber, and the first hollow, cavity slit or chamber may be adapted and arranged to receive one or more tissues samples, wherein the one or more tissues samples are in the form of one or more of a solid, a liquid, a suspension, and combinations thereof. Moreover, a three-dimensional matrix of the invention may comprises at least one second hollow cavity, slit or chamber, wherein each of the second hollows, cavities, slits or chambers is adapted and arranged to receive at least a portion of the additional source of nutrition.

Preferably, the three-dimensional matrix of the invention matrix comprises a gel, the gel being suitable for measuring at least one of the one or more parameters and of producing resulting data. Moreover, the physiological matrices of the present invention are adapted and arranged for measuring the efficacy of one or a plurality of therapeutic compounds, many of which are exemplified herein. Moreover, means or methods of the invention can be adapted and arranged to test the efficacy of non-synthetic chemical therapies, wherein the non-synthetic chemical therapies are one or more selected from the group comprising radiation therapies, brachiotherapies, herbal therapies, naturopathic therapies, experimental therapeutic compounds, and new therapeutic compounds, hyperthermal therapies, hyperbaric therapies, hypobaric and photosensitizing therapies.

An additional benefit of the present invention pertains to its amenability to kit form. Thus, in some embodiments, the invention may include a kit for testing the efficacy of therapeutic compounds on an expedited basis, the kit comprising a means for collecting at least one tissue comprising cells from an animal, the tissue being suspected of being abnormal, cancerous or pre-cancerous, at least one three-dimensional physiological matrix for culturing the tissue sample in three dimensions for a sufficient length of time to obtain measurements of at least one parameter of the behavior of the cells and the tissue, a means for measuring the parameters to determine a set of possible therapeutic compounds which might be efficacious for treating the tumor or abnormal tissue, and a means for testing the therapeutic effect of the determined therapeutic compounds.

Preferably, the behavior of cells at multiple sites, for example, at least 2 sites or at least 3 sites, or at least 4 sites, or at least 5 sites is measured to obtain data regarding the behavior of the tissue or cells. In some preferred embodiments, readings made using microscopy and video-microscopy include the actions or steps of measuring directly the migratory distance, speed, cell density and direction of movement of the cells or tissue with respect to the matrix upon which they are placed or cultured.

In other preferred embodiments of the invention, the suspect tissue and matrix are then processed and treated so that they can be snap frozen, paraffin embedded, sectioned, and then assessed with respect to one or more parameters, including, but not limited to, mitotic index/cell division, cell growth, necrosis, apoptosis, anoikis, adhesion, cellular signaling and invasion-related protein expression. Any number of protein and genetic parameters can be analyzed with respect to their usefulness in determining the oncologic state of the cells or tissues.

In accordance with certain other aspects of the invention, the matrix may be of any configuration or material which permits the evaluation of the effect of therapeutic compounds on the cells or tissues. In some embodiments of the invention, the matrix preferably comprises a collagen gel, the gel being suitable for measuring the one or more parameters. Matrices could include any protein or glycoprotein or sugar components of extracellular matrix, for example, including but not limited to, fibronectin, laminin, hylaronin, growth factors and integrins.

In general, in one set of preferred embodiments, the typical matrix element of the invention comprises a gel. In one set of especially preferred embodiments, a matrix of the invention comprises protein in its native, non-denatured state, in the amount of 1.0 to 2.1 mg/ml. One preferred protein is, for example, Type I Collagen. Other proteins are amenable to use or adaptation as components of matrices of the invention. In some embodiments, a matrix of the invention possesses a final pH preferably in the range of from 6.0 to 8.5, more preferably in the range of from 6.5 to 8.0, and most preferably in the pH range of from 6.8 to 7.5.

In other embodiments, a matrix of the invention is incubated and used in an air atmosphere having carbon dioxide preferably in the range of 1.0 to 18.0%, more preferably in the range of from 2.0 to 14.0%, and most preferably in the range of from 4.0 to 9.0%. A carbon dioxide incubator is useful for incubation processes according to the invention. In accordance with other aspects of the invention, the parameters of matrix composition, carbon dioxide tension, and other conditions vary according to tumor type. For example, for most categories of tumors, temperatures for incubation of the matrices combined with tissue or cells are generally kept within approximate physiological ranges, preferably of from 30-44 degrees Celsius, more preferably of from 33-41 degrees Celsius, and most preferably of from 35-39 degrees Celsius.

In another advantageous aspect of some embodiments of the invention, a matrix may comprise one or more constituents provided to adapt the matrix for use with a particular tumor, or a particular class of tumors. Possible constituents to a matrix according to the invention, for example a gel matrix, may include growth factors such as VEGF or HGF, which tends to alter the invasion patterns of the tissue cells into the matrix and enhances cell growth. Other possible constituents include structural proteins, for instance, extracellular matrix proteins like laminin, fibronectin, and the various collagens, for example Collagen IV.

Immunoglobulins may also be included or added to a matrix of the invention in order to stabilize it in various respects. For instance, anti-laminin may be included in the matrix. As additional means and methods for adapting matrices of the invention to uses with respect to specific tumors or classes of tumors, lipids, such as human or bovine brain extract, solids like human dura, and plant extracts such as phytostimulants and inhibitors may also be included in a matrix of the invention in order to vary its characteristics and adapt it to specific use. In some embodiments, other living cells may be included. Exemplary cells include melanoma cells, fibroblasts and endothelial cells.

Matrices of the invention may include inert additives also. As examples, glass or plastic shapes, such as cylinders may be provided within tissue culture wells to act as structural forms for the gel so that the matrix gel can be molded to create a tiny well or indentation useful for adding cell suspensions such as leukemia or lymphoma cells to the matrix in a pre-determined area in the matrix gels.

In accordance with preferred aspects of the invention, the one or more parameters to be measured comprise one or more of: the speed of proliferation of the cells, the speed of unidirectional migration of the cells, the speed of bi-directional migration of the cells, the speed of tri-directional migration of the cells, the rate of mitosis of the cells, the rate of change of migrational direction of the cells, the proportion of cells which change migrational direction during the test period, the speed of migrating cells in a particular visual field, the density of migrating cells per microscopic visual field, the migrational distance of individual migrating cells per microscopic visual field, the average migration-al distance of a group or population of migrating cells per microscopic visual field, and the number of migrating cells per microscopic visual field direction.

With respect to the invention, the "Test Period" is that period of time during which the one or more tissues or cells are cultured and tested with respect to their oncological behaviors, and the "Evaluational Period" is that period of time during which the one or more therapeutic compounds are evaluated with respect to efficacy in treating the specific tissue samples or cells, and other parameters.

In accordance with the many advantageous aspects of the methods of the invention, the one or more therapeutic compounds or treatments are selected from the group comprising, but not limited to, DNA damaging agents, anti-mitotics, cell cycle stimulators, anti-metastatics, anti-invasives, radiosensitizers, radiation, and any established, theoretical or experimental therapeutics against cell growth and cell invasion.

Methods of the invention include the evaluation of one or more therapeutic compounds, individually, combined with one another, as one or more cocktails, or in any sequence, in order to determine their likely efficacy against the suspected tumor tissue and cells. Thus, in some embodiments, the methods of the invention include testing one therapeutic compound, or a pair of therapeutic compounds, or three therapeutic compounds, or four therapeutic compounds, or more than four therapeutic compounds, or any number of compounds in a cocktail of compounds, or provided at different times or sequences to the tissue being evaluated.

Preferably, the culturing of the tissue and the cells during the test and evaluational periods is for a length of time sufficient to obtain the values required to make a determination of the efficaciousness of one or more potential therapeutic compounds. The culturing of the tissue and the cells occurs for a period sufficiently long enough to obtain the needed data. Thus, the culturing of the tissue and the cells occurs during the one or more test and evaluational periods, and thus during a period of time of preferably less than 10 days, more preferably of less than 8 days, even more preferably of less than 6 days, and most preferably of less than 4 days. Thus, all readings typically occur within 10 days from the time of removal of the tissue or cells from the mammal. Basic microscopic readings of distance, direction and density are taken manually or by automated systems, preferably at predetermined intervals depending on the nature of the suspected tumor, the nature and amount of the tissue and the nature and number of cells or cell types being evaluated. In accordance with the various embodiments of the invention, the predetermined interval is one or more hours, for example, every 4 hours, or every 8 hours or every 16 hours or every 24 hours.

Video monitoring of the tissues and cells may also be provided in order to gather and record additional information. The video monitoring is preferably provided on a continuous basis at intervals. The intervals are selected based upon the nature of the tissue and cells, the nature of the suspected tumor or tumors, and the estimation of likely behavior of the tissue and cells on a matrix. In some preferred embodiments of the invention, video monitoring is provided on a continuous basis, at 30-second intervals, or at 60-second intervals or at 90-second intervals or at 120-second intervals, or at 150-second intervals.

Methods of the present invention include also those of testing the efficacy of therapeutic compounds on an expedited basis, testing the efficacy of therapeutic compounds with respect to a specific individual mammal, such as a human, and testing the synergistic efficacy of two or more therapeutic compounds on an expedited basis.

The present invention includes also one or more kits for testing the synergistic efficacy of therapeutic compounds on an expedited basis, the kit comprising i) means for collecting at least one tissue comprising cells from a mammal, the tissue being suspected of being transformed into cancerous or pre-cancerous tissue, ii) means for culturing the tissue comprising cells for a sufficient length of time to obtain desired values, iii) means for evaluating the values to determine a set of possible therapeutic compounds which might be efficacious for treating the tumor, and iv) means for testing the therapeutic effect of the determined therapeutic compounds.

As one of skill in the oncology arts will appreciate, numerous variations of the means and methods disclosed herein fall within the scope of the present application. Moreover, the examples provided herein are provided as inclusive illustrations of the invention, and not as exclusive limitations.

DESCRIPTIONS OF THE FIGURES

FIGS. 1-8 are photographic and photomicrographic images which show, by way of example, use of the means and methods of the present invention with respect to a tissue sample removed from a patient. With respect to FIGS. 1-8, Patient Sample GS-640, comprising kidney tissue, was removed from the patient by a surgeon during surgery.

Tissue analysis and screening in accordance with the invention were requested by the surgeon, and proper consent was obtained from the patient prior to surgical removal of a sample quantity of tissue from the RHS Kidney. The patient was diagnosed with renal cell carcinoma. A tissue sample of approximately 1 gram in quantity was removed from the patient during surgery, and was placed into a 25 ml sample jar, and immersed in sterile saline. The tumor tissue was kept at 4 degrees centigrade until processed for the screening of therapeutic compounds in accordance with the means and methods of the invention. All procedures were performed under sterile conditions in a bio-safety laminar flow hood.

FIG. 1 is a photographic image showing the mechanical division of the sample into portions to be tested. The sample has been prepared by dissecting away any non viable tissue and blood prior to mincing into 1-2 mm pieces using sterile disposable scalpels.

Figure 2:
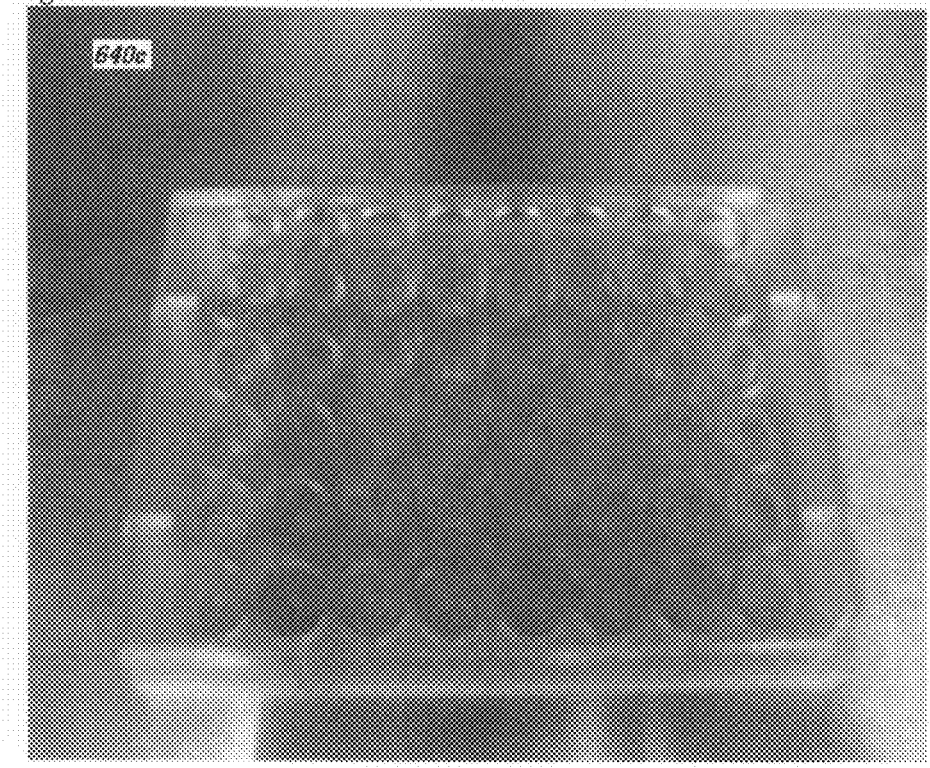

FIG. 2 is a photographic image showing tumor sample portions which have been placed into each well of a 48 well plate, and been submersed in a gel matrix mixture according to the invention. After insertion of the portions, the mixture was allowed to form into a gel at room temperature for approximately 30 minutes. Once the gel formed around the fully immersed tumor fragments, nutrient rich media was added as a liquid overlay that permeated the entire gel and tumor fragment.

Each different chemotherapy and or dose of chemotherapy was added to a set of 6 wells out of the 48-well plate. A total of 7 different chemotherapies were assessed in this plate. One set of six wells were not treated with drug and thus acted as 'control conditions' for tumor fragment growth and invasion. Each of the eight vertical lanes containing six separate wells was marked with a symbol for each chemotherapy/dose used and noted correspondingly on data collection sheets. FIG. 2 shows plate after chemotherapeutics and growth media have been added. The plates were then placed in a conventional 37 degree Celsius incubator at 5% $CO_2$.

Figure 3:
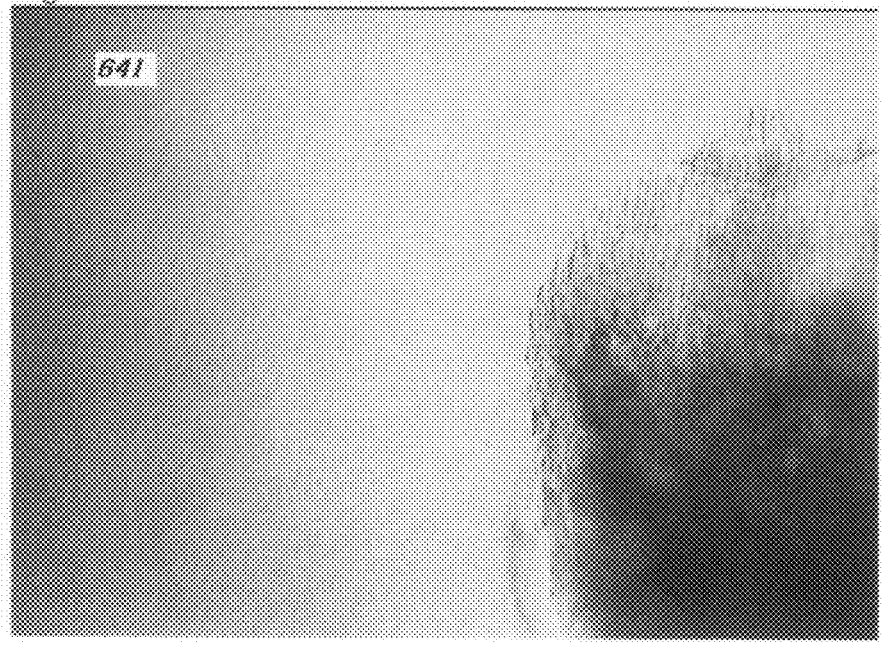

FIG. 3 is a photomicrographic image which shows the tumor sample at Day 0 where the initial appearance of the tissue fragment in the lower right of the photomicrograph shows no cell migration or invasion of cells away from the margins of the sample portion and out into the gel. This image is thus representative of all wells at Day 0 with or without chemotherapeutics. Images were made with a 400× magnification phase contrast micrograph using ZEISS camera specs.

Figure 4:
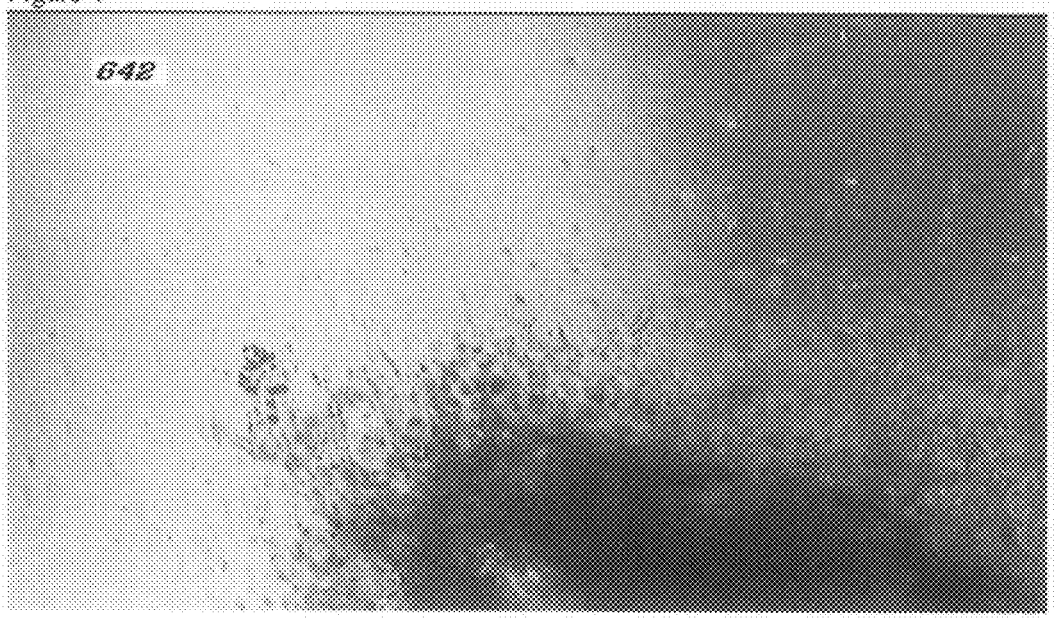

FIG. 4 is a photomicrographic image which showing a patient control sample (no treatment) after 3 days incubation @37° C. and 5% $CO_2$. Noteworthy is the migration of cells away from the solid tumor mass in a halo around the tumour fragment.

Figure 5:
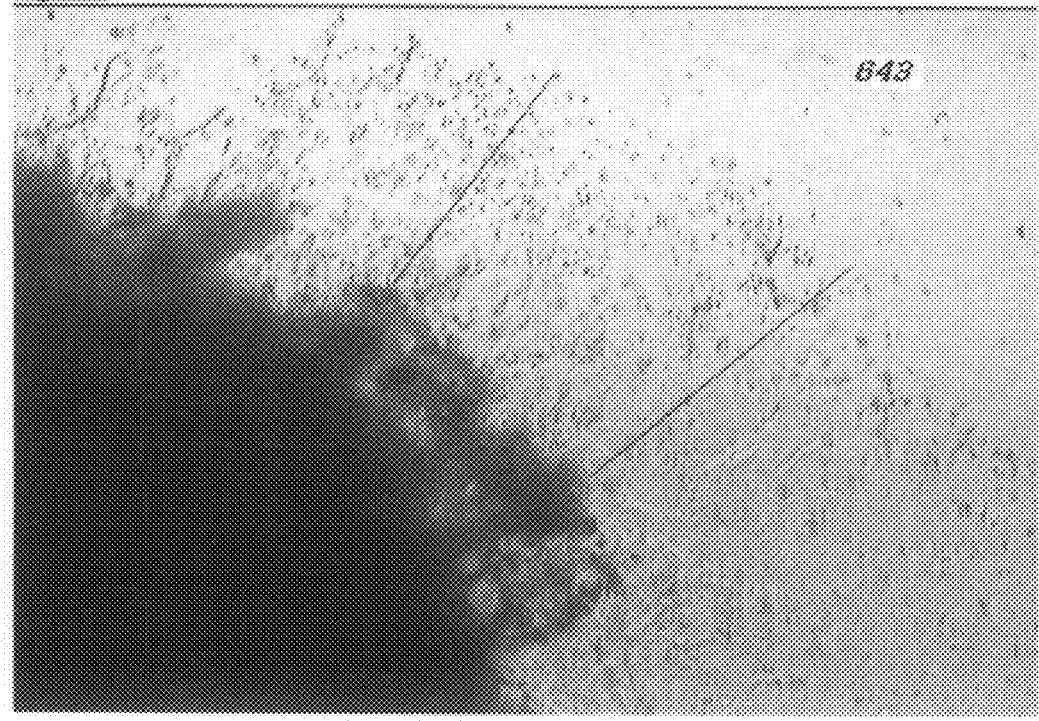

FIG. 5 is a photomicrographic image which shows a patient control sample after 5 days. Noteworthy is the halo of cells and increased cell density as compared with the results shown at Day 3 of the test. The lines on the images have been drawn to show the distance measurements within which approximately 95% of the migrating cells have migrated away from the margins of the tissue sample.

FIG. 5 also shows the presence of fibroblasts which sometimes appear at the later time points. Fibroblasts are noticeably different in numbers and appearance than migrating tumor cells. For example, fibroblasts appear in the surrounding gel matrix as much larger cells than the migrating tumor cells, and with significantly larger cytoplasm, as well as the classic elongated spindle fibroblast appearance. Fibroblasts also stain positively upon immuno-histochemical analysis for antibodies to fibroblast markers such as fibroblast growth factor. Thus, fibroblasts may be differentiated from tumor cells in a straightforward manner.

Figure 6:
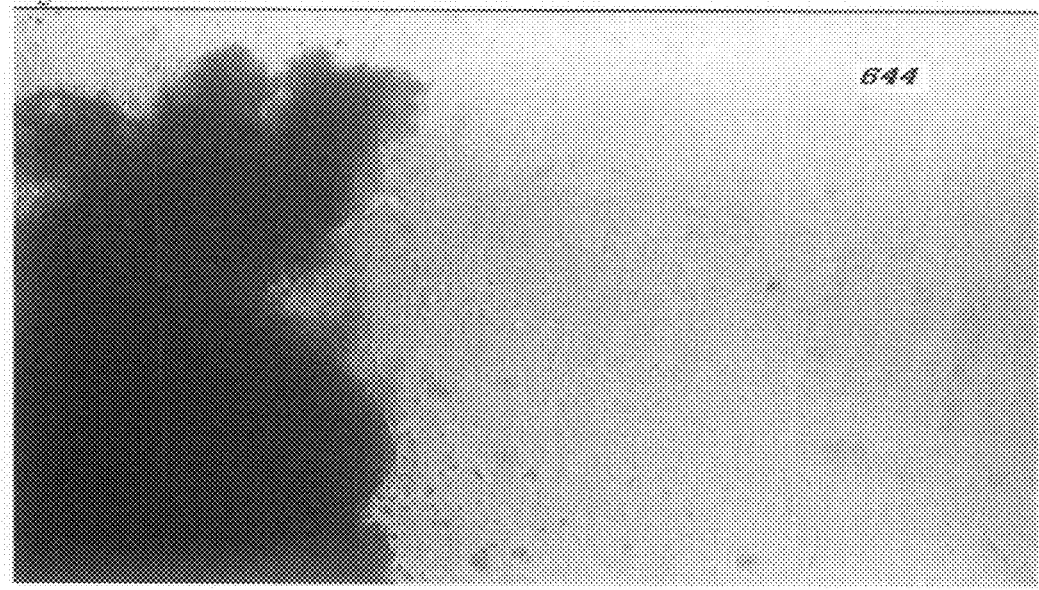

FIG. 6 is a photomicrographic image demonstrating the effect of treatment with Taxol™. The image of FIG. 6 shows a sample well at 5 days after treatment with Taxol™. Noteworthy is the change in behavior of the cells exposed to Taxol™. Specifically, a drop in both the distance and the number of cells that have grown and invaded away from the solid tumor fragment is seen on the lower left hand side of the image.

Figure 7:

FIG. 7 is a photomicrographic image which demonstrates the effect of treatment with Docetaxol™. The image of FIG. 7 shows a sample well wherein the tumor tissue has been treated for 5 days with Docetaxol™ while showing a moderate response to the drug. This moderate response is evidenced by the fewer number of invading cells than the control but those treated with Docetaxol™ have a longer migratory distance than treatment with Taxol™.

Figure 8:
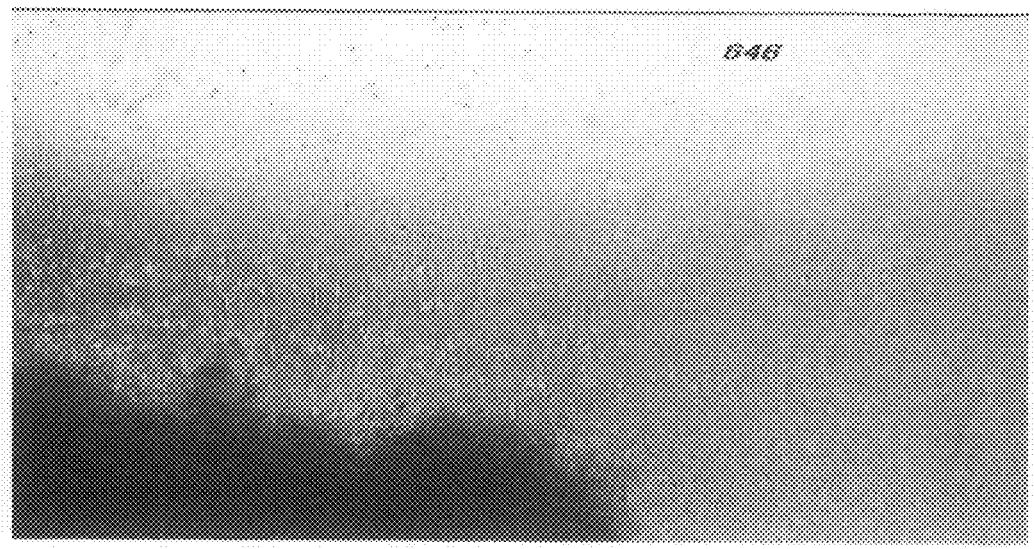

FIG. 8 is a photomicrographic image which shows the carcinoma patient sample treated for 5 Days with Cisplatin™. This image thus shows an example of a failed chemotherapy, being identical in appearance and cell numbers to the control sample (FIG. 5) at the same 5 day time point.

BRIEF DESCRIPTION OF THE TABLE

The present invention is adaptable to be used with many possible therapeutic substances, and combinations thereof, including those shown in the accompanying Table Of Exemplary Therapeutic Compounds. In accordance with important aspects of the invention, the attached Table provides only an exemplary list of therapeutic compounds which may be evaluated with the present methods and means. Virtually any other compound or combination of compounds with potential therapeutic value may be tested and evaluated with the present invention. Moreover, the means and methods of the present invention are adaptable and useful for testing any compound or combination of compounds with respect to their potential therapeutic value, regardless of whether those compounds have been involved in the drug approval process. Thus, the present invention provides means and methods for initially testing and evaluating compounds with respect to possible efficacy against many tumors and tumor types without the necessity of using animal or human subjects.

As those of skill in the art will appreciate, numerous permutations of the matrices, methods, apparatus and kits of the invention are possible within the metes and bounds of the information disclosed herein. Thus, although the present invention has been described with reference to some of the preferred embodiments, variations and modifications of steps, elements and components of the invention can be substituted therefore, while remaining within the spirit and scope of the invention.

TABLE OF EXEMPLARY THERAPEUTIC COMPOUNDS

| Quantitiy | Compound |
| --- | --- |
| 3 | TMZ 250 mg capsules (Scering) |
| 1 | Irinotecan 20 mg/ml solution × 5 ml vial (Pharmacia) |
| 1 | Procarbazine 50 mg capsule (Sigma-Tau) |
| 1 | Methotrexate 25 mg/ml solution × 20 ml vial (Mayne) |
| 1 | Carboplatin 10 mg/ml solution × 45 ml vial (Mayne) |
| 1 | Adriamycin 2 mg/ml solution × 100 ml vial (Novo) |
| 1 | Cisplatin 1 mg/ml solution × 100 ml vial (Mayne) |
| 1 | Vincristine 1 mg/ml solution × 5 ml vial (Mayne) |
| 1 | Paclitaxel 6 mg/ml solution × 50 ml vial (BMS) |
| 3 | CCNU 100 mg capsules (BMS) |
| 1 | BCNU powder for injection × 100 mg vial (BMS) |
| 1 | Cyclophosphamide powder for injection × 2 gm vial (BMS) |
| 1 | Docetaxel 40 mg/ml solution with diluent × 2 ml vial (Aventis) |
| 1 | 5FU 50mg/ml solution × 100 ml vial (Mayne) |
| 1 | Cytarabine 100 mg/ml soltuion × 10 ml vial (Mayne) |
| 1 | Cytarabine 100 mg powder for injection (Pfizer) |

What is claimed is:

1. A three dimensional physiological gel matrix suitable for incubating at least one tissue sample from an animal, said tissue sample comprising cells, wherein said cells or said tissue are suspected of being abnormal, cancerous, or pre-cancerous, wherein said physiological matrix comprises:

(A) wherein the physiological matrix comprises collagen fibers adapted and arranged such that the cells, if abnormal, cancerous or pre-cancerous, are enabled to grow away from the sample portion into the matrix, and wherein said collagen fiber is present in a density of from 1.3 mg/ml to 3.3 mg/ml, (B) a sufficient amount of at least one additive providing hydroxyl anions or protons to adjust the pH of the matrix into a range suitable for a particular tissue, cell or tumor, and C) nutrition sufficient to sustain said cells and said tissue in the matrix wherein said physiological matrix is formed from components which are essentially free of bicarbonate during the process of forming a gel.

2. The three-dimensional physiological matrix of claim 1, wherein said matrix is adapted and arranged to accept a tissue sample as the gel is being formed.

3. The three-dimensional physiological matrix of claim 1, wherein the collagen fibers are selected from the group consisting of type I collagen, type II collagen, type III collagen, type IV collagen and synthetic collagen-like fibers.

4. The three-dimensional physiological matrix of claim 1, wherein said additive is one or more of NAOH or KOH.

5. The three-dimensional physiological matrix of claim 1, further comprising additional nutrition to be added after the formation of the gel.

6. The three-dimensional physiological matrix of claim 5, wherein said additional nutrition comprises a tissue culture medium or concentrated tissue culture medium.

7. The three-dimensional physiological matrix of claim 6, wherein said concentrated medium is a 10× medium.

8. The three-dimensional physiological matrix of claim 5, wherein the additional nutrition comprises sera, proteins, sugars, salts and lipids.

9. The three-dimensional physiological matrix of claim 1, further comprising a tissue sample, wherein said tissue is completely submerged with said three-dimensional matrix.

10. The three-dimensional physiological matrix of claim 9, wherein said sufficient nutrition is supplemented with one or more of sera, proteins, sugars, salts and lipids.

11. The three-dimensional physiological matrix of claim 1, wherein said acceptable pH range is from 5.0 to 8.3.

12. The three-dimensional physiological matrix of claim 1, wherein said acceptable pH range is from 6.4 to 7.9.

13. The three-dimensional physiological matrix of claim 1, wherein said acceptable pH range is from 7.2 to 7.6.

14. The three-dimensional physiological matrix of claim 1, wherein the density of said fiber in said matrix is between 2.0 and 2.8 mgs/ml.

15. The three-dimensional physiological matrix of claim 1, wherein the density of said fiber in said matrix is between 2.3 and 2.5 mgs/ml.

16. The three-dimensional physiological matrix of claim 1, wherein said matrix is adapted and arranged to be suitable for measuring at least one parameter of the behavior of cells from said tissue, said at least one parameter relating to said suspected abnormal, cancerous or pre-cancerous status of said cells or said tissue.

17. The method of claim 16, wherein said one or more parameters comprises one or more of the distance which individual cells migrate from said tissue sample, the average distance of migration of a group or population of said cells from said tissue sample, the distance which individual cells migrate from said tissue sample with respect to time, the average distance of migration of a group or population of said cells from said tissue sample with respect to time, the velocity of migration of one or more designated individual said cells per selected time period, the velocity of migration of a group or population of designated said cells per selected time period, the number of migrational cells per unit area of a microscopic visual field, the speed of proliferation of said cells, the speed of unidirectional migration of said cells, the speed of bi-directional migration of said cells, the speed of tri-directional migration of said cells, the frequency of directional change of said migrating cells, the number of directional changes per unit time of said migrating cells, the rate of mitosis of said migrating cells, the number of cells migrating per unit time, the number of cells in a unit area of a portion of the gel, the change in the number of cells in a unit area of a portion of the gel with respect to time, the number of cells in a unit volume of a portion of the gel with respect to time, and the change in the number of cells in a unit volume of a portion of the gel, the proportion of cells which change migrational direction during the test period, the speed of migrating cells in a particular visual field, the density of migrating cells per unit area of a visual field, the migrational distance of individual migrating cells per unit area of a visual field, the average migrational distance of a group or population of migrating cells per unit area of a visual field, and the number of migrating cells in a particular direction per unit area of a visual field.

18. The three-dimensional physiological matrix of claim 1, wherein Type I collagen comprises at least 50% of said fiber.

19. The three-dimensional physiological matrix of claim 1, wherein Type I collagen comprises at least 70% of said fiber.

20. The three-dimensional physiological matrix of claim 1, wherein Type I collagen comprises at least 90% of said fiber.

21. The three-dimensional physiological matrix of claim 1, wherein Type I collagen comprises at least 95% of said fiber.

22. The three-dimensional physiological matrix of claim 3, wherein said collagen is Type I, wherein the at least one additive is NaOH, and wherein the sufficient nutrition is a bicarbonate-free 10× medium.

23. The three-dimensional physiological matrix of claim 1, wherein said matrix comprises at least one hollow, cavity, slit, chamber or slot, and wherein each said at least one hollow, cavity slit chamber or slot is adapted and arranged to receive a tissue sample.

24. The three-dimensional physiological matrix of claim 1, wherein said matrix comprises more than one hollow, cavity, slit, chamber or slot, and wherein each said more than one hollow, cavity slit chamber or slot is adapted and arranged to receive a tissue sample.

25. The three-dimensional physiological matrix of claim 9, wherein one or more tissue samples are in the form of a solid, a liquid, a suspension, or a combination thereof.

26. The three-dimensional physiological matrix of claim 1, wherein said physiological matrix is adapted and arranged for measuring the efficacy of one or more therapeutic compounds, and wherein said one or more therapeutic compounds are selected from the group comprising DNA damaging agents such as alkylating agents, antibiotics which affect nucleic acids, platinum compounds, anti-mitotics, cell cycle stimulators, anti-metastatics, anti-metabolites, camptothecin derivatives, hormone therapies, biological response modifiers, interferon, anti-invasives, radio-sensitizers, pro-mitotics, cell cycle inhibitors, pro-metastatics, pro-metabolites, anti-hormone therapies, pro-invasives, radiation, and any established, theoretical or experimental therapeutics directed for or against cell growth, cell invasion or cell viability.

27. The three-dimensional physiological matrix of claim 26, wherein said physiological matrix is adapted and arranged for measuring the efficacy of one or more therapeutic compounds, and wherein said one or more therapeutic compounds are selected from the group consisting of Temozolomide (TMZ), Irinotecan, Procarbazine, Methotrexate, Carboplatin, Adriamycin Cisplatin, Vincristine, Paclitaxel, 1-(2-chloroethyl)-3-cyclohexyl-1-nitrosourea (CCNU), carmustine (BCNU), Cyclophosphamide, Docetaxel, fluorouracil (5FU), Cytarabine, doxorubicin, bleomycin, topotecan, tamoxifen (TMX), and imatinib mesylate (Gleevec) and all other therapeutics clinically appropriate for treatment.

28. The three-dimensional physiological matrix of claim 1, wherein said one or more therapeutic compounds comprises at least two therapeutic compounds.

29. The three-dimensional physiological matrix of claim 26, wherein at least two therapeutic compounds are selected from CAF (Cyclophosphamide/Adriamycin, Fluorouracil); CMF (Cyclophosphamide/Methotrexate/Fluorouracil); CMFVP (Cyclophosphamide/Methotrexate/Fluorouracil/Vincristine/Prednisone); PCV (Procarbazine/CCNU/Vincristine); ICARBO-E (Isosfamide/Carboplatin/Etoposide); TAP (Taxol/Adriamycin/Cisplatin); EMA-CO (Etoposide/Methotrexate/Actinomycin/CyclophosphamideNincristine); VBP(Vinblastine/Bleomycin/Platinol); BPD-T (BCNU/Platinol/Dacarbazine/Tamoxifen); or T-10 (Methotrexate/BleomycinCyclophosphamide/Dactinomycin/Adriamycin).

30. The three-dimensional physiological matrix of claim 1, wherein said matrix is adapted and arranged to test the efficacy of non-synthetic chemical therapies, wherein said non-synthetic chemical therapies are one or more selected from the group comprising radiation therapies, brachiotherapies, herbal therapies, naturopathic therapies, experimental therapeutic compounds, new therapeutic compounds, hyperbaric therapies, hypobaric therapies, hypothermal therapies, hyperthermal therapies, and photosensitizing therapies.

31. The three-dimensional physiological matrix of claim 1, wherein said matrix is formed to comprise said sufficient nutrition.

32. The three-dimensional physiological matrix of claim 1, wherein said matrix is formed to comprise said additional nutrition.

33. The three-dimensional physiological matrix of claim 1, wherein said matrix is formed in multiple containers such that multiple portions of said sample can be evaluated.

34. The three-dimensional physiological matrix of claim 1, wherein said matrix is formed in multiple containers and said multiple containers comprise a multi-well plate or apparatus.

35. A kit for incubating one or more tissue samples, said kit comprising
(I) means for collecting at least one tissue from an animal, said tissue comprising cells, said tissue or cells suspected for being cancerous, abnormal or pre-cancerous,
(II) components sufficient to for at least one three-dimensional physiological matrix for incubating said tissue, wherein said matrix comprises
(a) collagen fibers adapted and arranged such that the cells, if abnormal, cancerous or pre-cancerous, are enabled to grow away from the sample portion into the matrix, and wherein said collagen fiber is present in a density of from 1.3 mg/ml to 3.3 mg/ml,
(B) a sufficient amount of at least one additive providing hydroxyl anions or protons to adjust the pH of the matrix into a range suitable for a particular tissue, cell or tumor, and
C) nutrition sufficient to sustain said cells and said tissue in the matrix for a length of time to obtain measurements of at least one parameter of the behavior of said cells and said tissue,
and wherein said components are essentially free of bicarbonate.

36. The kit of claim 35, wherein said at least one three-dimensional physiological matrix is provided as multiple matrices, and wherein said matrices are in sufficient number such that multiple portions of said one or more tissue samples can be incubated concurrently or sequentially in said matrices.

37. The kit of claim 35, wherein said at least one parameter comprises one or more of: the distance which individual cells migrate from said tissue sample, the average distance of migration of a group or population of said cells from said tissue sample, the distance which individual cells migrate from said tissue sample with respect to time, the average distance of migration of a group or population of said cells from said tissue sample with respect to time, the velocity of migration of one or more designated individual said cells per selected time period, the velocity of migration of a group or population of designated said cells per selected time period, the number of migrational cells per unit area of a microscopic visual field, the speed of proliferation of said cells, the speed of unidirectional migration of said cells, the speed of bi-directional migration of said cells, the speed of tri-directional migration of said cells, the frequency of directional change of said migrating cells, the number of directional changes per unit time of said migrating cells, the rate of mitosis of said migrating cells, the number of cells migrating per unit time, the number of cells in a unit area of a portion of the gel, the change in the number of cells in a unit area of a portion of the gel with respect to time, the number of cells in a unit volume of a portion of the gel with respect to time, and the change in the number of cells in a unit volume of a portion of the gel, the proportion of cells which change migrational direction during the test period, the speed of migrating cells in a particular visual field, the density of migrating cells per unit area of a visual field, the migrational distance of individual migrating cells per unit area of a visual field, the average migrational distance of a group or population of migrating cells per unit area of a visual field, and the number of migrating cells in a particular direction per unit area of a visual field.

38. The kit of claim 35, adapted and arranged for testing the efficacy of one or more possible therapeutic compounds, and wherein said one or more therapeutic compounds are selected from the group consisting of DNA damaging agents such as alkylating agents, antibiotics which affect nucleic acids, platinum compounds, anti-mitotics, cell cycle stimulators, anti-metastatics, anti-metabolites, camptothecin derivatives, hormone therapies, biological response modifiers, interferon, anti-invasives, radio-sensitizers, pro-mitotics, cell cycle inhibitors, pro-metastatics, pro-metabolites, anti-hormone therapies, pro-invasives, radiation, any established, theoretical or experimental therapeutics directed for or against cell growth, cell invasion or cell viability, Temozolomide (TMZ), Irinotecan, Procarbazine, Methotrexate, Carboplatin, Adriamycin Cisplatin, Vincristine, Paclitaxel, 1-(2-chloroethyl)-3-cyclohexyl-1-nitrosourea (CCNU), carmustine (BCNU), Cyclophosphamide, Docetaxel, fluorouracil (5FU), Cytarabine, doxorubicin, bleomycin, topotecan, tamoxifen (TMX), and imatinib mesylate (Gleevec) and all other therapeutics clinically appropriate for treatment.

39. The kit of claim 35, wherein said kit is adapted and arranged to test the efficacy of non-synthetic chemical therapies, wherein said non-synthetic chemical therapies are one or more selected from the group consisting of radiation therapies, brachiotherapies, herbal therapies, naturopathic therapies, experimental therapeutic compounds, new therapeutic compounds, hyperbaric therapies, hypobaric therapies, hypothermal therapies, hyperthermal therapies, and photosensitizing therapies.

40. The three-dimensional physiological matrix of claim 9, wherein sufficient nutrition is provided to said tissue after said sample has been placed in the matrix, wherein said matrix has been equilibrated to a temperature of from 10 degrees Celsius to 30 degrees Celsius.

41. The three-dimensional physiological matrix of claim 3 wherein the physiological matrix further comprises one or more of fibrin, fibrinogen, extracellular matrix proteins derived from one or more animals, laminin, fibronectin, anti-laminin or synthetic collagen-like fibers.

* * * * *